United States Patent [19]

Gordon

[11] Patent Number: 5,417,673
[45] Date of Patent: May 23, 1995

[54] WHOLE BLOOD SAMPLE NEEDLELESS SAMPLE SITE

[75] Inventor: Mark G. Gordon, Tustin, Calif.

[73] Assignee: Medex, Inc., Hilliard, Ohio

[21] Appl. No.: 231,982

[22] Filed: Apr. 21, 1994

Related U.S. Application Data

[63] Continuation of Ser. No. 3,790, Jan. 13, 1993, abandoned.

[51] Int. Cl.[6] .................................. A61M 25/00
[52] U.S. Cl. ............................ 604/283; 604/86
[58] Field of Search ................ 604/82, 86–88, 604/201, 244, 249, 256, 283, 905; 228/760, 762, 763, 764

[56] References Cited

U.S. PATENT DOCUMENTS

| | | |
|---|---|---|
| 3,057,350 | 6/1958 | Cowley . |
| 3,613,663 | 10/1971 | Johnson . |
| 3,620,500 | 11/1971 | Santomieri . |
| 3,752,510 | 8/1973 | Windischman et al. . |
| 3,837,381 | 9/1974 | Arroyo . |
| 4,390,346 | 6/1983 | Cramer et al. . |
| 4,647,212 | 3/1987 | Hankison . |
| 4,838,858 | 6/1989 | Wortham et al. . |
| 4,842,591 | 6/1989 | Luther . |
| 4,846,794 | 7/1989 | Hertzer . |
| 4,874,369 | 10/1989 | Kulle et al. ............... 604/86 |
| 4,874,377 | 10/1989 | Newgard et al. . |
| 4,895,346 | 1/1990 | Steigerwald . |
| 4,911,705 | 3/1990 | Heinzerling et al. ........ 604/86 |
| 4,915,687 | 4/1990 | Sivert . |
| 4,935,009 | 6/1990 | Caldwell et al. . |
| 4,935,010 | 6/1990 | Cox et al. . |
| 4,960,412 | 10/1990 | Fink . |
| 4,967,797 | 11/1990 | Manska . |
| 5,114,400 | 5/1992 | Lynn ........................ 604/905 |
| 5,135,492 | 8/1992 | Melker et al. ............ 604/86 |
| 5,178,607 | 1/1993 | Lynn et al. ............... 604/86 |
| 5,203,775 | 4/1993 | Frank et al. .............. 604/256 |

FOREIGN PATENT DOCUMENTS

| | | |
|---|---|---|
| 0314856 | 1/1988 | European Pat. Off. . |
| 0309771 | 3/1988 | European Pat. Off. . |
| 0462814 | 12/1991 | European Pat. Off. . |
| WO9011103 | 10/1990 | WIPO . |
| WO9100115 | 1/1991 | WIPO . |
| WO9204936 | 4/1992 | WIPO . |

OTHER PUBLICATIONS

Baxter Vamp Brochure 170000-2 Rev. A (6 pp.) (1989).
Baxter Vamp Brochure 106865-2, Rev. A. (4 pp.) (1989).
U.S. Application Serial No. 07/746,239, filed Aug. 15, 1992, entitled Sample Site with Flow Directors.

*Primary Examiner*—John D. Yasko
*Assistant Examiner*—Manuel Mendez
*Attorney, Agent, or Firm*—Wood, Herron & Evans

[57] ABSTRACT

A whole blood sample needleless sample site includes a flow diverter between the ports and below the seal member to divert fluid away from the normal flow path between the ports and up towards the underside of the seal member to thereby flush same.

31 Claims, 3 Drawing Sheets

WHOLE BLOOD SAMPLE NEEDLELESS SAMPLE SITE

This application is continuation of application Ser. No. 08/003,790 filed Jan. 13, 1993, and now abandoned.

BACKGROUND OF THE INVENTION

1. Field of the Invention

The present invention relates to needleless sample sites through which fluids are injected or withdrawn from a patient's circulatory system and, more particularly, to such a sample site through which a whole blood sample may be taken.

2. Description of the Prior Art

Sample sites typically comprise a housing through which fluids flow and which is in-line with tubing connected to a patient's circulatory system. Blood may be withdrawn through the sample site by inserting a needle or the blunt canula tip of a syringe, for example, into the housing through a seal in the sample site housing and withdrawing the fluid inside the housing.

An exemplary system which may advantageously employ a sample site for withdrawing blood is a blood pressure monitoring system in which a catheter inserted into a patient's blood vessel is connected via tubing to a blood pressure sensor, and a stopcock, which either connects the tubing to a supply of saline solution or a reservoir. A sample site may be included in-line with the tubing blood sampling without an additional needle puncture to the patient.

When the tubing is connected through the stopcock to the saline source, the sensor is in fluid communication with the patient's circulatory system to sense the patient's blood pressure. When it is desired to take a sample of the patient's blood, rather than puncturing the patient with another needle, the sample site may be used. To this end, the stopcock is turned to disconnect the saline source from the patient's circulatory system to the reservoir. Saline will flow away from the patient and into the reservoir as the patient's blood flows through the tubing and into and through the sample site. Thereafter the needle of a syringe or the syringe tip itself is inserted into the sample site and blood is withdrawn therefrom with the syringe. The needle or syringe tip is then removed from the sample site after which the stopcock is turned to disconnect the patient's circulatory system from the reservoir, reestablishing the connection between the patient's circulatory system and the saline source so as to reestablish the blood pressure monitoring function.

When using a sample site as in the above-described system, it is desirable that whole blood be removed from the patient through the sample site. That is, it is desirable that the blood removed through the sample site not be mixed with any other fluid, such as the saline solution normally present in the sample site during blood pressure monitoring. Where the sample site is for needle-based use, such as where the seal is a latex plug that only a needle may pierce (i.e., a blunt cannula is not usable), all of the saline may be displaced from inside the housing during a sampling operation by the use of flow directors in the sample site inlet and/or outlet port(s) as described in co-pending application Ser. No. 07/746,239, filed Aug. 15, 1991, the disclosure of which is incorporated by reference as if set forth fully herein. While such port-located flow directors are believed to provide undiluted whole blood samples for needle-based systems, port-located flow directors may not always be sufficient to flush the sample site in non-needle-based or needleless systems due to the operation of the seal and any related valve structure.

SUMMARY OF THE INVENTION

The present invention provides a sample site for non-needle-based systems (i.e., where a blunt cannula is to be used to access the sample site) which minimizes or eliminates the likelihood that saline will remain in the sample site to dilute the blood sample.

As will be appreciated, a typical sample site includes a pair of tubular ports disposed on opposite sides of the housing and through which fluid may flow past the seal and between the ports. Typical of needleless system is that the seal is resilient and deflectable so that it opens under pressure of blunt cannula against the topside of the seal. To provide room for the seal to deflect and open, the seal is typically held within a cylinder extending above and out of the main fluid path. As a result, blood flowing through the sample site may not flush the saline out from the cylinder. The remaining saline solution may thus dilute the blood sample when the sample is withdrawn from the cavity.

In some cases, the seal is part of an actuator valve assembly such as that shown in commonly assigned U.S. application Ser. No. 07/855,147 filed Mar. 20, 1992, which is a continuation of Ser. No. 07/584,286 filed Sep. 18, 1990, the disclosures of both of which are also incorporated by reference as if fully set forth herein. With the valved type of device as there shown, the seal is held above and out of the normal fluid flow path by a solid obturator member with a fluid lumen therethrough and through which blood and saline, for example, pass between the ports and the seal. With that type of arrangement, the lumen cannot, as a practical matter, by flushed of saline (or other undesired fluids such as from an earlier sample) merely by fluid flowing into and back out of the sample site through the ports resulting in undesirably diluted blood samples.

To this end, and in accordance with the principles of the present invention, the needleless sample site is modified to include flow diverters between the ports and spaced below the underside of the seal. The flow diverters are placed in the otherwise main flow path and thus interrupt the flow to divert fluid upwardly against the backside of the seal to flush the adjacent area, leaving only whole blood in the sample site and, importantly, in the area below the seal. The flow diverter maybe an upstanding wall molded into the sample site sample site and may further include an angled portion to divert the fluid flowing into the cavity from one port upwardly toward the bottom side of the seal. Alternatively, the flow diverter may be defined by an inverted U-shaped channel interconnected with the ports with the bite portion of the channel exposed to the seal underside. This type of arrangement "jets" fluid up against the seal underside and is particularly useful to jet fluid through the lumen in the solid obturator of the valved sample site. In either case, the result is to provide a pair of liquid paths extending between the seal underside and the respective ports such that fluid is directed to the underside of the seal to flow thereacross and flush all of the saline out of the sample site after which a whole blood sample may be drawn.

The flow diverters may be bidirectional so that the sample site may be inserted in-line without regard to which port is on the patient or saline side of the system. The bidirectional nature of the flow directors also provides reverse flushing action. Thus, when the pressure monitoring system is to be reestablished after a blood sample is taken, all of the remaining blood will be flushed back into the patient's circulatory system. To this end, the flow diverter causes the fluid to flow up against the seal irrespective of whether the fluid is flowing into the cavity from one port or the other.

By virtue of the foregoing, there is thus provided a whole blood sample needleless sample site which does not suffer from a dead space to dilute or otherwise interfere with obtaining a whole blood sample through the sample site.

These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION OF THE DRAWINGS

Figure 1:
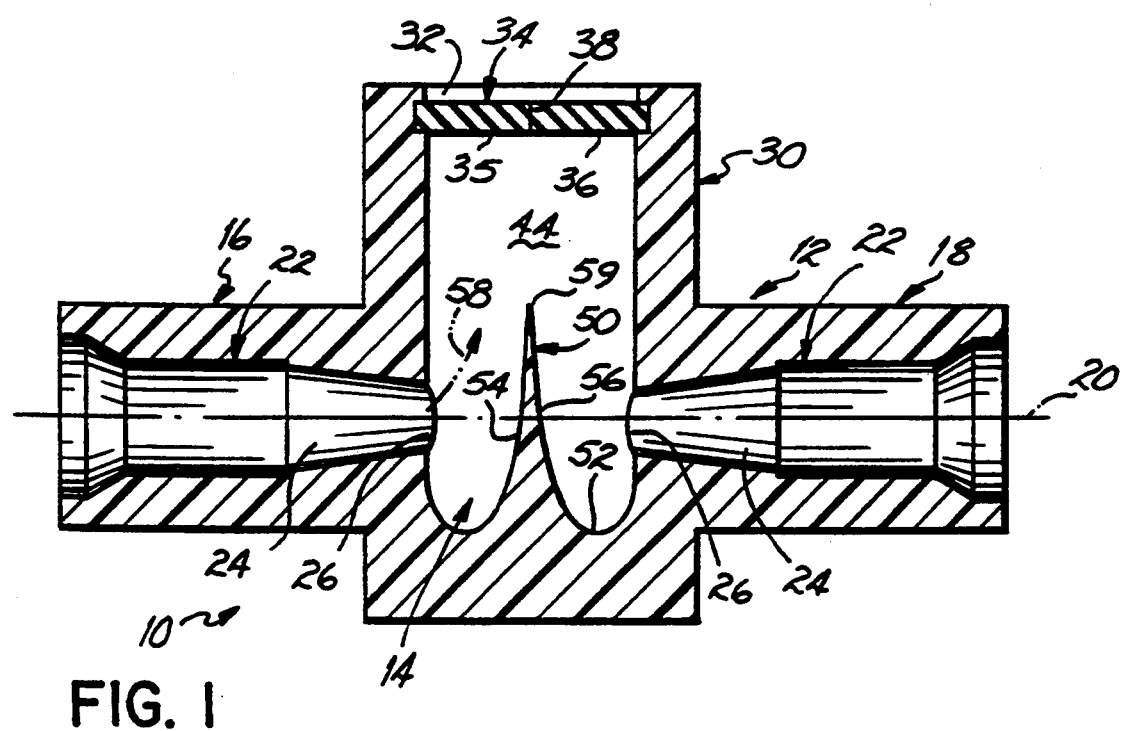
FIG. 1 is a cross-sectional view of one embodiment of a whole blood sample needleless sample site constructed in accordance with the principles of the present invention.

With reference to FIG. 1, there is shown a cross-section of one embodiment of a whole blood sample needleless sample site 10 in accordance with the principles of the present invention. Sample site 10 includes a plastic (e.g. polycarbonate) housing 12 defining a fluid cavity 14 therein and between a pair of tubular or cylindrical ports 16, 18 connected to opposite sides of the housing 12 such as along common axis 20. The interior walls 22 of ports 16, 18 may taper as at 24 to provide smaller diameter circular openings for inlets 26 to cavity 14.

Figure 2:
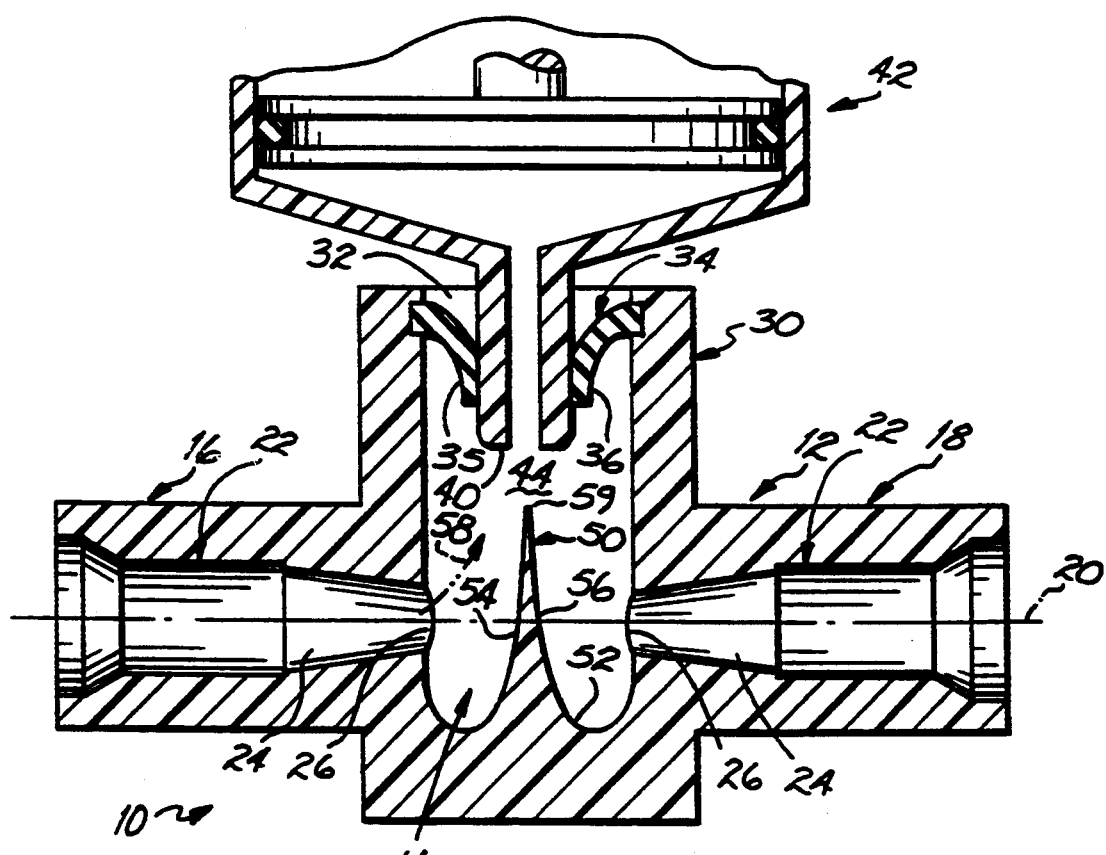
FIG. 2 is a cross-sectional view of the sample site of FIG. 1 shown with the blunt tip end of a syringe accessing the site.

Fluid cavity 14 extends above common axis 20 into cylindrical portion 30 of housing 12. Mounted to cylinder 30, and spanning aperture 32 at the end thereof, is a seal member 34, comprised, for example, of a pair of resilient wings 35, 36 which normally are in contact to close and seal aperture 32 along slit 38. Aperture 32 is sized to receive a blunt cannula. As seen in FIG. 2, when a blunt cannula such as the tip end 40 of a syringe 42 presses against seal wings 35, 36, they separate along slit 38 and deflect into portion 30 to allow tip end 40 to pass therethrough into fluid communication with cavity 14. A sample of fluid 44 in cavity 14 may then be taken with syringe 42. Thereafter, tip end 40 is removed and wings 35, 36 return to the position shown in FIG. 1 to again seal aperture 32.

To avoid the otherwise likely possibility that fluid may pool below seal member 34 in the area of cylindrical portion 30 and not be flushed out by fluid entering through one of ports 16 or 18 thus possibly leading to diluted blood samples, flow diverter 50 is molded into housing 12 and extends to the bottom 52 of cavity 14 as an upstanding vertical wall through the center of cavity 14 generally aligned with slit 38. Diverter 50 is generally perpendicular to common axis 20 and transverse to the underside of seal member 34 to interrupt flow directly between ports 16 and 18 along common axis 20. To divert fluid towards seal member 34, diverter 50 supports surface 54 confronting inlet 26 of port 16 and angled relative the vertical, as well as an oppositely angled or inclined surface 56 confronting inlet 26 of port 18. As a consequence, fluid flowing into cavity 14 from port 16, for example, impinges against surface 54 and is directed upwardly (as represented by arrow 58) into cylindrical portion 30 towards or against the back side of seal member wings 35 and 36 flushing fluid therefrom and out through port 18. The area below the seal member is thus flushed clean by the entering fluid so that a whole blood sample may be taken where the entering fluid is whole blood for example.

Diverter 50 is bidirectional by provision of angled or inclined surfaces 54, 56 on both sides of diverter 50 facing the respective ports 16 and 18. Surfaces 54, 56 thus provide an inverted U-shaped flow path, the legs of which couple to ports 16, 18 and the bite portion of which is exposed (such as along distal edge 59 of diverter wall 50) to seal member 34. Thus, fluid flowing into cavity 14 from either port 16 or port 18 will flush the area within cylindrical portion 30 behind seal member 34. Although not shown, it will be readily appreciated that ports 16, 18 could include male and female Luer connectors. Similarly, a Luer connector, or split-Luer such as shown in aforementioned application Ser. No. 07/855,147 could be provided about aperture 32 and seal member 34 to receive any sort of blunt cannula such as a male Luer slip or a locking male Luer connector.

Figure 3:
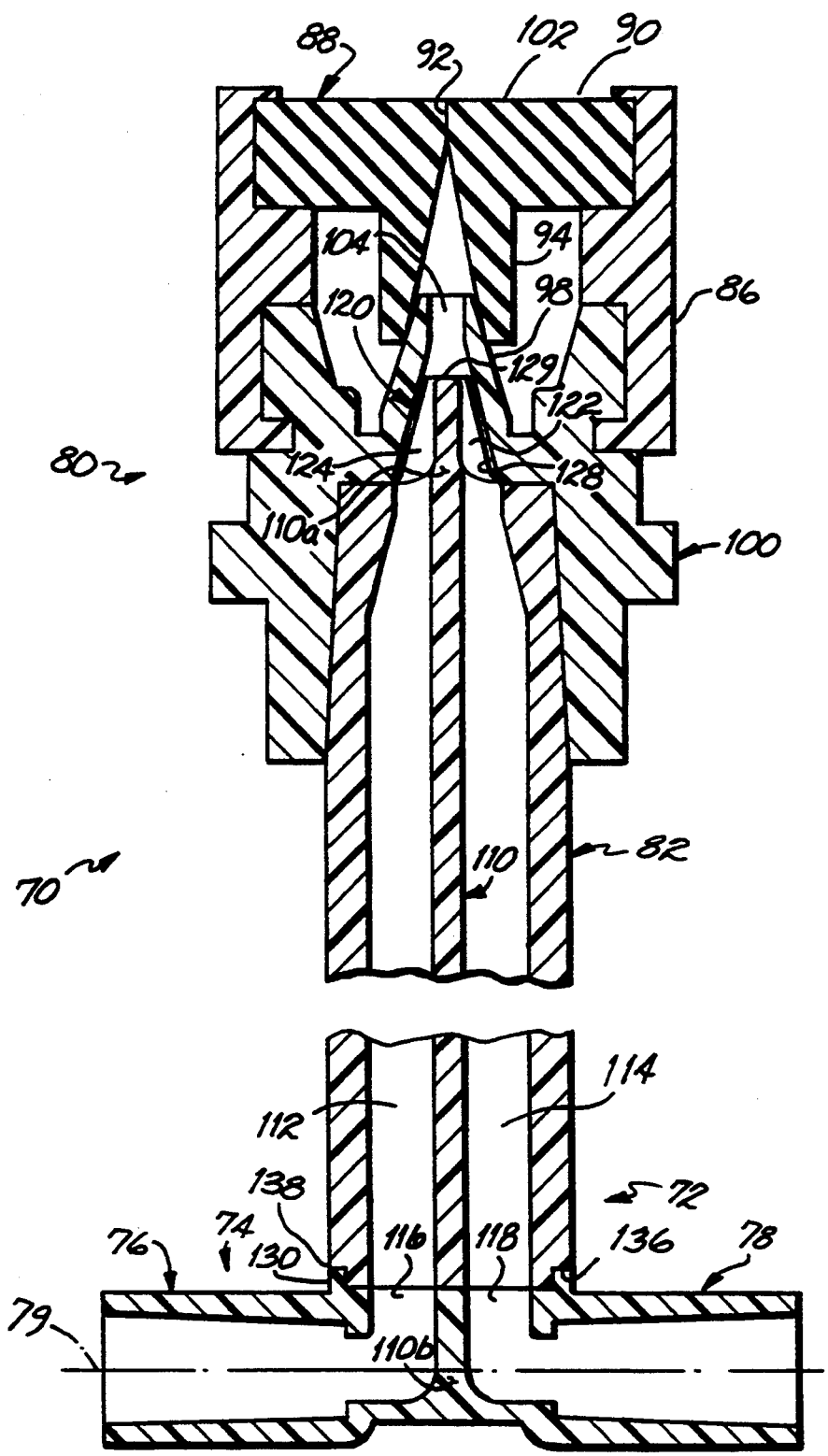
FIG. 3 is a cross-sectional view of another embodiment of a whole blood needleless sample site constructed in accordance with the principles of the present invention.

With reference to FIG. 3, There is shown another embodiment of a whole blood sample needleless sample site 70 shown in cross-section. Sample site 70 is comprised of housing 72 having a base portion 74 supporting at opposite ends thereof first and second fluid ports 76 and 78 along common axis 79, valve assembly portion 80, and hub portion 82 therebetween for communicating fluid between valve assembly portion 80 and ports 76, 78. As in the case of ports 16 and 18 of sample site 10, ports 76 and 78 may be provided with a female Luer and a male taper respectively (both not shown).

With respect to valve assembly portion 80, housing shell 86 supports a resilient seal member 88 spanning aperture 90. Seal member 88 includes a central channel 92 which is normally closed as shown in FIG. 3. Seal member 88 includes an underside tapered hub 94 which sits astride frustro-conical tip 98 of obturator member 100. Obturator member 100 and shell 86 are held together such as by glue. Aperture 90 is sized to receive a blunt cannula therethrough, such as the previously mentioned tip end 40 of syringe 42. When the blunt cannula is pressed against upper surface 102 of seal member 88, seal member 88 deflects toward obturator member 100 and drives hub 94 against the conical surface of tip 98. As hub 94 rides over tip 98, channel 92 is caused to open revealing lumen 104 of obturator 100 for fluid communication with the blunt cannula. When the blunt cannula is removed, the resiliency of seal member 88 causes hub 94 to ride up tip 98 and reseal channel 92.

In sample sites having the obturator/seal member arrangement as above described, such as shown in aforementioned application Ser. No. 07/855,147, fluid would normally flow directly between ports 76, 78 such as along common axis 79. Consequently, fluid, such as saline, within the lumen would not typically be flushed out of the lumen by the fluid flowing between the ports. Under the circumstances, when a whole blood sample is attempted with a blunt cannula through aperture 90, some of the old fluid, such as saline, may be present in lumen 104. The result would be a diluted blood sample. To avoid such a problem, as in the case of sample site 10, sample site 70 includes a flow diverter 110 comprised of upper core 110a within hub portion 82 and lower core 110b within base portion 74, which together are similar to upstanding wall 50 of sample site 10. More specifically, diverter 110 is situated between ports 76, 78 and is tangent to channel 92 to separate fluid conduits 112, 114 defined through hub portion 82 and pipes 116, 118 defined in base portion 74, respectively. Conduits 112, 114 and pipes 116, 118 cooperate to divert fluid passing between ports 76 and 78 off of common axis 79. Instead, fluid is directed into conduits 112, 114 and towards obturator lumen 104.

Core 110a extends into central projection 120 at its distal extremity. Central projection 120 is tapered (see FIG. 4) to expose the upper ends of conduits 112, 114 as cylindrical reliefs or recesses 122, 124, respectively. Projection 120 is sized to fit within tapered recess 128 formed in obturator member 100 below lumen 104 so as to surround recesses 122, 124 such that fluid flowing up through either conduit 112 or 114 is directed, or "jetted", into lumen 104, over the tip 129 of projection 120 and then back down the other conduit to thereby flush lumen 104. As will be appreciated, conduits 112, 114 form the legs of an inverted U-shaped channel with the distal end 120 defining an exposed bite portion thereof.

Figure 4:
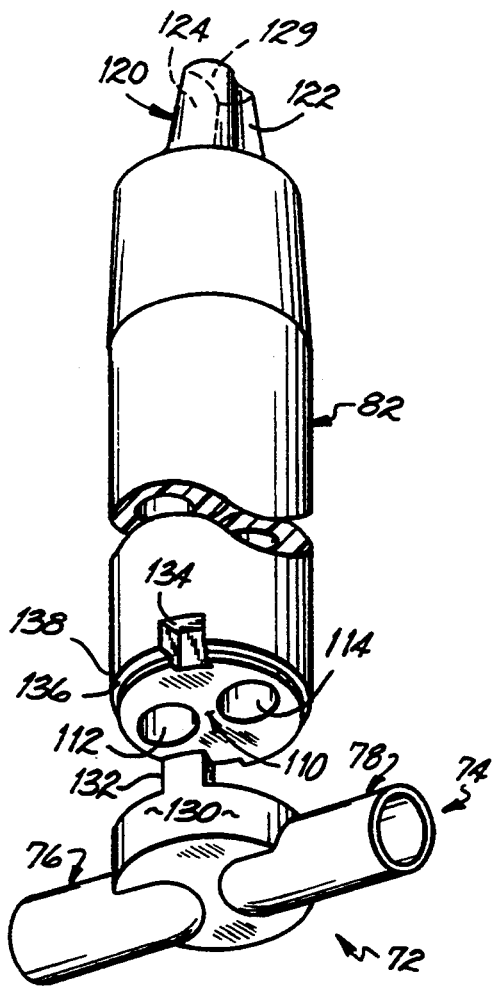
FIG. 4 is a perspective exploded view of the base and hub portions of the sample site of FIG. 3.
Figure 5:
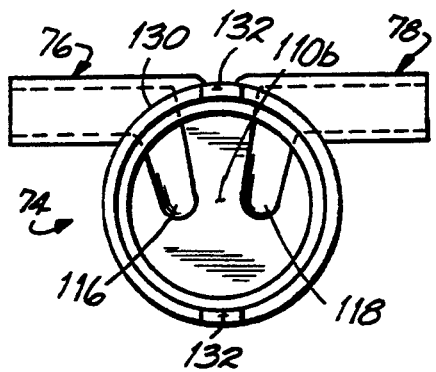
FIG. 5 is a top view of an alternative base portion for the sample site of FIG. 3.

To connect base portion 74 and hub portion 82, as seen in FIG. 4, base portion 74 includes cylindrical wall 130 surrounding pipes 116, 118. Wall 130 includes an upstanding tab 132 which mates with recess 134 formed at the base of hub portion 82 to align the conduits 112, 114 and pipes 116, 118, respectively. Hub portion 82 includes an annular lip 136 about its proximal edge 138 which seats within (and may be glued to) wall 130 when tab 132 and recess 134 are aligned. Note that in FIG. 4, ports 74 and 76 are aligned on the diameter whereas they may be offset therefrom as seen in FIG. 5, to allow for a split-Luer clip member (not shown) to fit over sample site 70. In the offset arrangement as shown in FIG. 5, pipes 116 and 118 are extended and exposed.

As fluid enters port 76, for example, it is diverted by pipe 116 up into conduit 112 of hub portion 82 and over recess 124 and tip 129 of distal end 120 into lumen 104 to flush same. The flushed fluid is forced down over recess 122 into conduit 114, through pipe 118 and out of port 78. The above arrangement is bidirectional such that fluid flowing into site 70 through port 78 and out from out 76 follows the opposite path yet still flushes lumen 104.

Although the housing of both sample sites 10 and 70 have been shown as T-shaped in cross-section, the flow diverter of the present invention may be provided in other types of sample sites. Thus, for example, the ports (16 and 18 or 76 and 78) could form part of a Y-connector rather than a T-connector.

Figure 6:
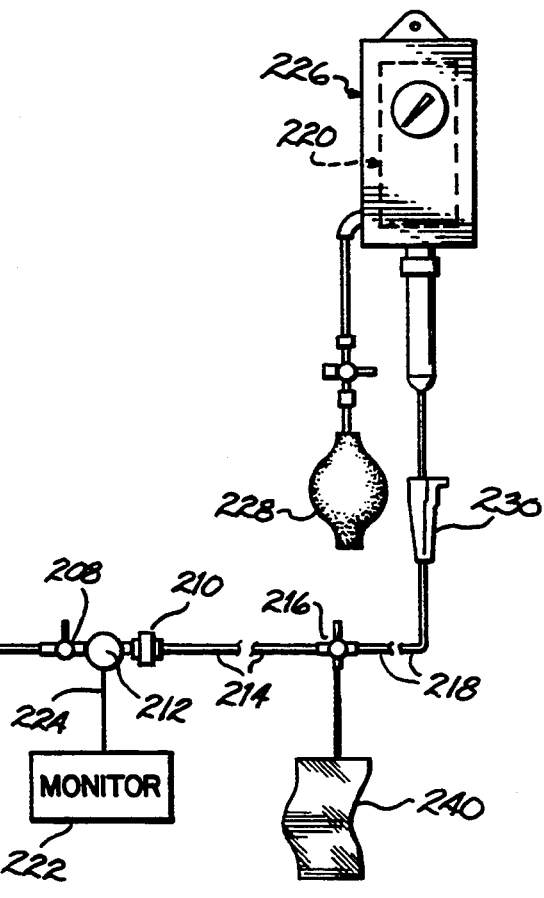
FIG. 6 is a diagrammatic view of an exemplary, closed pressure monitoring blood sampling system incorporating a sample site of the present invention for purpose of explaining the principles of operation of the present invention.

Needleless sample sites constructed in accordance with the present invention, such as sample site 10 or sample site 70, may be utilized for blood sampling as will now be described with reference to the exemplary closed blood pressure monitoring/blood sampling system 200 shown in FIG. 6. System 200 may be as described in commonly assigned U.S. Pat. No. 5,148,811, the disclosure of which is fully incorporated herein by reference. As seen in FIG. 6, catheter 202 inserted into a patient's blood vessel is connected by tubing 204 to port 16 of sample site 10 (or port 76 of sample site 70). The other port 18 (or 78) is connected via tubing 206 to stopcock 208 and flush valve 210. Intermediate stopcock 208 and flush valve 210 is a pressure sensor 212. Flush valve 210 is connected via tubing 214 to stopcock 216 and thence via tubing 218 to a source 220 of saline. As a consequence, when stopcocks 208 and 216 are properly positioned, sample site 10 (or 70) is in-line between saline source 220 and catheter 202 so that saline may flow therethrough and allow blood pressure monitoring by blood pressure sensor 212. Sensor 212 is coupled to blood pressure monitor 222 via sensor leads 224 as is well understood. As is also well known, saline source 220 may be pressurized by pressure infuser 226 and its associated squeeze bulb 228 and may also be flow controlled through roller clamp 230.

In use, when it is desired to obtain a blood sample, stopcock 216 is operated to connect catheter 202 to reservoir 240 through stopcock 216 which also disconnects catheter 202 from saline source 220. Blood from the patient will then flow out of catheter 202 and towards reservoir 240 pushing saline ahead of the blood. As the blood flows into and through sample site 10 (or 70), it will flow into port 16 (or 76) and be diverted by the flow diverter therein and away from common axis 20 (or 79) and up towards the backside of seal member 34 (or into and through lumen 104 of sample site 70) to flush out the saline 44 otherwise normally in that area until only whole blood remains, undiluted by saline. Stopcock 208 may then be manipulated to stop further flow of fluid and a whole blood sample taken by putting tip end 40 of syringe 42, for example, against the surface of the seal member 34 (or 88) to deflect and thus open same to allow fluid communication through tip end 40 of fluid within the sample site. The blood sample may then be withdrawn by manipulation of syringe 42 as is well known.

After the sample is taken and tip end 40 withdrawn, the seal member 34 (or 88) returns to its normal closed position. Thereafter, stopcocks 208 and 216 may be manipulated to restore the catheter-to-saline source connection causing blood remaining in system 200 downstream of stopcock 216 to be driven back into the patient. Blood mass loss is minimized further by the reverse flow of saline into sample site 10 (or 70) through port 18 (or 78) with a flushing action on the blood similar to the saline flush action above describe.

Although not shown, a female Luer connector (or wings) maybe positioned over the seal member 34 or 88 to allow a locking blunt cannula, such as a male slip having a locking cuff, to be locked onto the sample site to maintain the connection.

By virtue of the foregoing, there is thus provided a needleless sample site from which a whole blood sample may be reliably taken.

While the present invention has been illustrated by the description of embodiments thereof, and while the embodiments have been described in considerable detail, it is not the intention of applicant to restrict or in any way limit the scope of the appended claims to such detail. Additional advantages and modifications will readily appear to those skilled in the art. It will be understood that the sample site of the present invention may be utilized as an injection site when coupled to the venous side of a patient's circulatory system, as a sample port when connected to the arterial side, or as a link to connect an exterior fluidic system to an otherwise closed fluid system without opening the closed system, thereby avoiding the possibility of reflux in the closed system. Reference to sample site will thus be appreciated as a reference to any of the above. The invention in its broader aspects is therefore not limited to the specific details, representative apparatus and method, and illustrative examples shown and described. Accordingly, departures may be made from such details without departing from the spirit or scope of applicant's general inventive concept.

What is claimed is:

1. A sample site adapted to be accessed by a blunt cannula comprising:
   a housing having a bottom;
   a seal including a pair of resilient wing members spaced above the housing bottom and being openable and deflectable into the housing under pressure of the blunt cannula thereagainst whereby to selectively access fluid inside the housing;
   a pair of ports connected to the housing and having inlets in fluid communication with the inside of the housing, the inlets having a bottom edge and a top edge; and
   flow diverter means between the ports and extending from the port inlet bottom edge to the port inlet top edge to completely interrupt a line of sight path between the port inlets, the flow diverter means being spaced from the wing members so as to direct fluid towards the wing members as fluid flows into the housing from one of the ports to the other port.

2. The sample site of claim 1, the flow diverter means including a wall extending generally perpendicular to the ports.

3. The sample site of claim 1, the flow diverter means supporting an angled surface confronting one of the ports.

4. The sample site of claim 1, the flow diverter means supporting a pair of oppositely angled surfaces confronting respective ones of the ports.

5. The sample site of claim 1, the flow diverter means including means defining an inverted U-shaped channel the respective legs of which are coupled to respective ones of the ports and the bite portion of which is aimed at the seal wherein the bite portion is exposed for fluid communication with the seal.

6. A sample site adapted to be accessed by a blunt cannula comprising:
   a housing having a bottom;
   a pair of ports connected for fluid communication into and out of the housing;
   an obturator member fixedly positioned within the housing and having a lumen therethrough in fluid communication with the ports;
   an apertured exterior wall on the housing through which the blunt cannula can enter the housing to make fluid connection to the lumen;
   seal means adjacent the exterior wall aperture for normally sealing the aperture against fluid communication with the lumen, the seal means being movable into the obturator member under pressure of the blunt cannula passing into the aperture so as so open a channel in the seal means and expose the lumen therethrough to the blunt cannula; and
   means extending at least partially into the obturator lumen for defining first and second separate flow paths between the obturator member lumen and respective ones of the ports.

7. The needleless sample site of claim 6 wherein the housing includes base means for supporting the ports and hub means for defining at least a portion of the first and second flow paths extending from the obturator member lumen.

8. The needleless sample site of claim 7, the hub means including a central projection having a pair of recess means thereon for defining portions of the flow paths adjacent the lumen.

9. The needleless sample site of claim 8, the obturator member having means for receiving the central projection such that the obturator member surrounds the recess means.

10. The needleless sample site of claim 7, the base means including pipe means for coupling each of the flow paths to respective ones of the ports.

11. The needleless sample site of claim 7, the hub means including a pair of conduit means therethrough for defining the respective flow paths.

12. The sample site of claim 11, the base means including pipe means for coupling each of the flow paths to respective ones of the ports, the base means and the hub means being separate components and including cooperating positioning means for aligning the pipe means and the conduit means.

13. The sample site of claim 7, the base means and the hub means being separate components.

14. The sample site of claim 6 wherein the means defining the first and second separate flow paths extends to the housing bottom.

15. The sample site of claim 7 wherein the housing bottom is in the base means and wherein the means defining the first and second separate flow paths includes a wall extending within the base means.

16. The sample site of claim 15 wherein the means defining the first and second separate flow paths further includes an extension of the base means wall extending into the hub means.

17. A sample site adapted to be accessed by a blunt cannula comprising:
   a housing;
   a resilient apertured seal member, and an obturator member fixed in the housing and having a lumen therethrough for fluid communication with the seal member, the seal member being openable by the obturator member under pressure of the blunt cannula thereagainst whereby to selectively access fluid inside the housing;
   a pair of ports connected to the housing in fluid communication with the inside of the housing; and
   an inverted U-shaped channel the respective legs of which are coupled to respective ones of the ports and the bite portion of which is aimed at the seal member wherein the bite portion is exposed for fluid communication with the seal member, the exposed bite portion of the U-shaped channel being coupled to the obturator lumen.

18. A sample site adapted to be accessed by a blunt cannula comprising:
a housing having a bottom and a cylindrical sidewall defining an open fluid cavity inside the housing;
a seal having a resilient member across the fluid cavity opening and spaced above the housing bottom, the resilient member being openable under pressure of the blunt cannula thereagainst whereby to selectively access fluid in the fluid cavity;
a pair of ports connected to the housing and having inlets in fluid communication with the fluid cavity, the inlets having a bottom edge and a top edge; and
a flow diverter situated within the fluid cavity and between the ports, the flow diverter extending from the port inlet bottom edge to the port inlet top edge to completely interrupt a line of sight path between the port inlets, the flow diverter having a generally flat distal edge extending completely across the fluid cavity from one end to an opposite end of the cylindrical sidewall of the housing and being spaced from the seal resilient member so as to direct fluid towards the seal resilient member as fluid flows into the housing from one of the ports to the other port.

19. The sample site of claim 18, the flow diverter including a wall extending generally perpendicular to the ports.

20. The sample site of claim 18, the flow diverter supporting an angled surface confronting one of the ports.

21. The sample site of claim 18, the flow diverter supporting a pair of oppositely angled surfaces confronting respective ones of the ports.

22. The sample site of claim 18, the seal resilient member including a pair of wings being deflectable into the housing under pressure of the blunt cannula thereagainst.

23. The sample site of claim 18, the flow diverter including means defining an inverted U-shaped channel the respective legs of which are coupled to respective ones of the ports and the bite portion of which supports the distal edge and is aimed at the seal resilient member wherein the bite portion is exposed for fluid communication with the seal.

24. A sample site adapted to be accessed by a blunt cannula comprising:
a housing having a bottom and a cylindrical sidewall defining an open fluid cavity inside the housing;
a seal having a resilient member across the fluid cavity opening and spaced above the housing bottom, the resilient member being openable under pressure of the blunt cannula thereagainst whereby to selectively access fluid in the fluid cavity;
a pair of ports connected to the housing and having inlets in fluid communication with the fluid cavity, the inlets having a bottom edge and a top edge; and
a flow diverter situated within the fluid cavity and between the ports, the flow diverter extending from the port inlet bottom edge to the port inlet top edge to completely interrupt a line of sight path between the port inlets, wherein no portion of the housing sidewall extends toward the flow diverter and the flow diverter is spaced from the seal resilient member, such that no portion of the resilient member contacts the flow diverter.

25. The sample site of claim 24, the flow diverter including a wall extending generally perpendicular to the ports.

26. The sample site of claim 24, the flow diverter supporting an angled surface confronting one of the ports.

27. The sample site of claim 24, the flow diverter supporting a pair of oppositely angled surfaces confronting respective ones of the ports.

28. The sample site of claim 24, the seal resilient member including a pair of wings being deflectable into the housing under pressure of the blunt cannula thereagainst.

29. The sample site of claim 24, the flow diverter having a generally flat distal edge extending completely across the fluid cavity from one end to an opposite end of the cylindrical sidewall of the housing.

30. The sample site of claim 24, wherein the port inlet edges are spaced from the housing bottom and wherein the flow diverter extends from the housing bottom such that the fluid cavity includes a portion below the port inlet bottom edge.

31. A sample site adapted to be accessed by a blunt cannula comprising:
a housing having a bottom and a cylindrical sidewall defining an open fluid cavity inside the housing;
a seal having a resilient member across the fluid cavity opening and spaced above the housing bottom, the resilient member being openable under pressure of the blunt cannula thereagainst whereby to selectively access fluid in the fluid cavity;
a pair of ports connected to the housing and having inlets in fluid communication with the fluid cavity, the inlets having a bottom edge and a top edge both being spaced from the housing bottom;
a flow diverter situated within the fluid cavity and between the ports, the flow diverter extending from the housing bottom across the port inlet bottom edge to the port inlet top edge to completely interrupt a line of sight path between the port inlets such that the fluid cavity includes a portion below the port inlet bottom edge.

* * * * *